United States Patent
Lumpkin et al.

(10) Patent No.: US 7,947,023 B1
(45) Date of Patent: *May 24, 2011

(54) METHOD AND APPARATUS FOR DISPOSABLE ASPIRATOR CASSETTE

(75) Inventors: Christopher F. Lumpkin, Steamboat Springs, CO (US); Shawn P. Mullen, Glenmoore, PA (US); John E. Richmond, Doylestown, PA (US); Michael D. Auld, Flemington, NJ (US)

(73) Assignee: Peregrine Surgical, Ltd., New Britain, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/807,714

(22) Filed: Sep. 13, 2010

Related U.S. Application Data

(62) Division of application No. 12/658,068, filed on Feb. 2, 2010, now Pat. No. 7,833,206.

(51) Int. Cl.
*A61M 1/00* (2006.01)
*A61M 37/00* (2006.01)

(52) U.S. Cl. .................. 604/319; 604/131; 604/541

(58) Field of Classification Search .............. 604/8–10, 604/30–3, 131, 152–153, 317–323, 326, 604/541, 543
See application file for complete search history.

(56) References Cited

U.S. PATENT DOCUMENTS

| | | | |
|---|---|---|---|
| 3,866,608 A | 2/1975 | Reynolds et al. | 604/319 |
| 4,058,123 A | 11/1977 | May | 604/30 |
| 4,359,051 A | 11/1982 | Oczkowski | 604/344 |
| 4,475,904 A | 10/1984 | Wang | 604/119 |
| 4,522,623 A | 6/1985 | Lauterjung | 604/319 |
| 4,627,833 A | 12/1986 | Cook | 604/34 |
| 4,735,610 A | 4/1988 | Akkas et al. | 604/119 |
| 4,758,238 A | 7/1988 | Sundblom et al. | 604/319 |
| 4,773,897 A | 9/1988 | Scheller et al. | 604/34 |
| 4,913,698 A | 4/1990 | Ito et al. | 604/22 |
| 4,963,131 A | 10/1990 | Wortrich | 604/34 |
| 5,078,677 A | 1/1992 | Gentelia et al. | 604/6.15 |
| 5,163,900 A * | 11/1992 | Wortrich | 604/30 |
| 5,242,404 A | 9/1993 | Conley et al. | 604/119 |
| 5,282,787 A * | 2/1994 | Wortrich | 604/30 |
| 5,302,093 A | 4/1994 | Owens et al. | 417/474 |
| 5,342,313 A | 8/1994 | Campbell et al. | 604/153 |
| 5,499,969 A * | 3/1996 | Beuchat et al. | 604/30 |
| 5,518,378 A | 5/1996 | Neftel et al. | 417/477.2 |
| 5,542,918 A | 8/1996 | Atkinson | 604/27 |
| 5,588,815 A | 12/1996 | Zaleski, II | 417/477.2 |
| 5,676,530 A | 10/1997 | Nazarifar | 417/360 |

(Continued)

FOREIGN PATENT DOCUMENTS

EP 0893603 B1 10/2002

*Primary Examiner* — Leslie R Deak
*Assistant Examiner* — Philip R Wiest
(74) *Attorney, Agent, or Firm* — Watov & Kipnes, P.C.; Kenneth Watov

(57) ABSTRACT

A known disposable per use surgical primary cassette is modified to avoid contamination thereof during use by aspirated fluid from a vitreous cutter connected thereto by bypassing the aspirated fluid into a receiving chamber of a relatively less expensive disposable secondary cassette, whereby during use a vacuum produced in a chamber of the primary cassette connected to the receiving chamber of the secondary cassette in turn produces a vacuum in the receiving chamber of the latter for drawing aspirated fluid from the vitreous cutter directly into the receiving chamber.

16 Claims, 9 Drawing Sheets

U.S. PATENT DOCUMENTS

| | | | |
|---|---|---|---|
| 5,676,650 A | 10/1997 | Grieshaber et al. | 604/28 |
| 5,718,568 A | 2/1998 | Neftel et al. | 417/476 |
| 5,741,125 A | 4/1998 | Neftel et al. | 417/477.7 |
| 5,782,611 A | 7/1998 | Neftel et al. | 417/234 |
| 5,788,671 A | 8/1998 | Johnson | 604/131 |
| 5,800,396 A | 9/1998 | Fanney et al. | 604/151 |
| 5,810,766 A | 9/1998 | Barnitz et al. | 604/34 |
| 5,876,387 A | 3/1999 | Killian et al. | 604/319 |
| 5,899,674 A | 5/1999 | Jung et al. | 417/477.2 |
| 6,059,544 A | 5/2000 | Jung et al. | 417/477.2 |
| 6,561,999 B1 | 5/2003 | Nazarifar et al. | 604/30 |
| 6,635,028 B1 | 10/2003 | Ielpo et al. | 604/27 |
| 6,780,166 B2 | 8/2004 | Kanda et al. | 604/30 |
| 6,824,525 B2 | 11/2004 | Nazarifar et al. | 604/30 |
| 6,899,694 B2 | 5/2005 | Kadziauskas et al. | 604/35 |
| 6,921,385 B2 | 7/2005 | Clements et al. | 604/141 |
| 6,948,918 B2 | 9/2005 | Hansen | 417/395 |
| 7,001,356 B2 | 2/2006 | Kadziauskas et al. | 604/35 |
| 7,160,268 B2 | 1/2007 | Darnell et al. | 604/141 |
| 7,540,855 B2 * | 6/2009 | Lumpkin et al. | 604/131 |
| 7,833,206 B1 * | 11/2010 | Lumpkin et al. | 604/319 |
| 2004/0115068 A1 | 6/2004 | Hansen et al. | 417/379 |
| 2005/0131361 A1 | 6/2005 | Miskie | 604/350 |

* cited by examiner

METHOD AND APPARATUS FOR DISPOSABLE ASPIRATOR CASSETTE

RELATED PATENT AND APPLICATION

The present invention is related to U.S. Pat. No. 7,540,855, entitled "Disposal Aspirator Cassette," dated Jun. 2, 2009, the teachings of which are incorporated herein to the extent they do not conflict herewith. The present Application is a Divisional from prior application Ser. No. 12/658,068, filed Feb. 2, 2010, now U.S. Pat. No. 7,833,206 entitled "Method And Apparatus For Disposable Aspirator Cassette."

FIELD OF THE INVENTION

The present invention is related broadly to aspirating systems, and more particularly to such systems including disposable cassettes for receiving aspirated fluid from a site being irrigated, such as but not limited to a surgical site.

BACKGROUND OF THE INVENTION

Many surgical systems require instruments and devices that provide for the use of fluids to irrigate surgical sites, and further provide for the aspiration of the fluids from the surgical sites, typically on a continuous or selectively intermittent process during the surgery. In many such prior systems, surgical cassettes are used to collect fluid aspirated from the surgical sites, whereby after use, due to contamination from the fluids, the now contaminated cassettes are typically disposed of. Many of the known cassettes are very expensive, and represent increased surgical costs for hospitals, and other health providers that must use such cassettes. There has been a long felt need in the art to provide devices or mechanisms for preventing the contamination of expensive surgical cassettes, thereby permitting continuous use of the primary cassette during multiple surgeries, to offer substantial cost savings to the health providers.

A vitrectomy is an example of a common surgical procedure performed for retinal eye disorders that typically requires use of the aforesaid surgical systems. More specifically, a vitrectomy is performed to remove vitreous humor (jelly-like liquid) from the posterior segment or back of eye. To maintain the integrity of the eye while vitreous is being aspirated, balanced salt solution is continually infused into the surgical site.

To perform a vitrectomy, the retinal surgeon uses one type of the aforesaid surgical systems known as a vitrectomy "unit." The vitrectomy unit serves as a "source pump" and/or "vacuum pump". Disposable components and instruments such as a Vitreous Cutter (cutter), Tubing Sets (tubing) and Cassette Reservoir (cassette) are attached to the vitrectomy unit. Together, the vitrectomy unit and disposable components make up a vitrectomy "system."

The vitrectomy unit itself is usually a large stand alone device that is not sterile, and is activated by the surgeon using a foot pedal. The disposable vitreous cutter is physically held by the surgeon and placed into the eye. When the vitrectomy unit is activated, vitreous and other bodily fluids are aspirated through the cutter and tubing, and ultimately are collected within the cassette.

The cassette is usually not handled by the surgeon during the operation. Rather, a circulating nurse preoperatively secures the cassette to the vitrectomy unit. The cassette has three primary functions. First, relative to one example in the prior art, because of its special proprietary design, it allows the vitrectomy unit to activate.

In most vitrectomy units, a cassette is required for activation. The cassette is generally produced as a disposable component. Prior to the start of each vitrectomy, a new cassette is opened and installed in the vitrectomy unit. A new cassette is used because in each case the previously used cassette is contaminated from eye fluids. After the vitrectomy, the cassette is then thrown away per hospital protocol regarding bio-contamination.

Second, once the vitrectomy unit is activated by inserting the proprietary cassette, the surgeon is then permitted to control vacuum and/or aspiration flow rate via use of a foot pedal. Fluids may now be vacuumed and or/aspirated out of the eye via the cutter and carried away through the tubing for deposit into the cassette. Typical cassette designs include features that maintain a constant fluidic resistance, to assist the physician in maintaining control of the aspiration flow rates through the cutter.

Third, in addition to the first and second functions, the cassette is specially designed with proprietary features to ONLY activate a proprietary vitrectomy unit for which it was designed. Therefore, use of a certain vitrectomy unit is dependent upon using the same company's proprietary cassette. This is how companies generate residual sales after selling a one time purchase of the vitrectomy unit.

An example of one such prior surgical cassette of a vitrectomy system is disclosed in Jung et al. U.S. Pat. No. 6,059,544, entitled "Identification System For A Surgical Cassette," issued on May 9, 2000. As shown in FIGS. 1 and 2 hereof, the cassette 10 includes a single piece plastic housing 12 that has a handle 44 for installing and removing the cassette 10 from a vitrectomy unit (not shown). The cassette 10 is a relatively complicated device, as described in the aforesaid patent. Certain, but not all of the features of cassette 10 will now be described. A cassette identification system 34 consists of a plurality of tabs 36 for identifying the cassette when it is plugged into an associated vitrectomy unit. With further reference to FIGS. 1 and 2, cassette 10 further includes aspiration lines 18 and 20, a peristaltic pump tube 16 having one end connected to an output port 30. A drain bag 14 is provided, and includes holes 32 to allow it to hang from hooks 26 provided on the cassette 10. A port 28 of the drain bag 14 is secured to an output port 30 associated with peristaltic pump tube 16. The drain bag 14 further includes a one-way valve 22 for preventing the backup of fluid into the cassette 10, and a sampling port 24 for permitting a sample of fluid to be drawn from the bag for testing, or other purposes. The cassette 10 further includes a first vacuum port 13, and a second vacuum port 15, as shown. Aspirator line 18 is connected between port 13 and a vacuum port 66. Aspirator line 20 is connected between port 15 and another vacuum port 68. Note both the cassette 10, and its associated drain bag 14, are provided by Alcon Laboratories, Inc., of Fort Worth, Tex. Due to the obvious complexity of the cassette 10, it represents a relatively high cost component for users, that must be disposed of after a first use, along with the associated drain bag or bags 14. Note that chamber 64 provides for receiving materials or aspirated liquid (contaminated eye fluid) drawn into chamber 64 through aspiration lines 18 and 20 by a vacuum produced in chamber 64 via vacuum input port 21 being connected to a vacuum source of the associated vitrectomy unit.

Alcon Laboratories, Inc. provides the cassette 10 in what they identify as a Total Plus Pack. The latter includes the cassette 10 along with a number of other disposable components.

The present inventors recognized that if a system is developed for permitting users of the aforesaid cassette 10, modified for use in the present system, to continually use the cassette, considerable cost savings will be provided. Accordingly, as described in detail below, the present inventors developed a system including a disposable surgical cassette that is substantially inexpensive relative to the cost of surgical cassettes such as the modified Cassette 10, whereby the present inventive surgical cassette is disposable, while permitting extended continuous use of the modified cassette 10 when used in association therewith. However, the present invention is not limited to permitting continual use of the aforesaid modified Alcon cassette 10, and can be used in other aspirating systems. For example, it is expected that the present inventive cassette will also have use in surgical aspirating systems in both posterior and anterior surgical fields. In addition, it is expected that the present inventive cassette will have use in industrial systems.

SUMMARY OF THE INVENTION

The inventors have developed a system including a unique secondary cassette having one application for vitrectomy surgeries that can adapt to a wide range of vitrectomy units. This cassette is used in addition to a modified primary cassette already installed on the vitrectomy unit. During a vitrectomy, the new secondary cassette protects the modified primary cassette from contamination, and therefore the latter can be continually used in successive surgical procedures.

The present secondary cassette has several functions. First, it acts as a reservoir for eye fluids so as not to allow contamination of known primary cassettes. Second, it works in tandem with existing primary cassettes to maintain a vacuum system for removal of vitreous and fluids. Third, the secondary cassette can be configured to collect a greater volume of aspiration fluids (greater capacity) than afforded by the primary cassette alone.

In one embodiment of the invention, the present system and secondary cassette is set up and operates in the following manner. Plastic tubing is attached to two separate ports located on one end of the secondary cassette. Tubing from one modified port of the primary cassette is attached to a vitreous cutter hand piece and extrusion instrument. Tubing from one port of the secondary cassette is attached to a new vacuum port of the modified primary cassette. Tubing from the other port of the secondary cassette is attached to a new aspirator port of the modified primary cassette, the latter being connected by tubing to the modified port of the primary cassette attached to the vitreous cutter.

Using a foot pedal, a surgeon activates the vitrectomy unit to generate suction as needed. Suction is created by the vitrectomy unit at the new vacuum port of the modified primary cassette. When this occurs a vacuum is formed in the secondary cassette, for causing intraocular fluids to be aspirated into the cutter tip, therefrom through the tubing attached to the one modified new aspirator port of the primary cassette, and therefrom through aforesaid tubing and the other port of the secondary cassette, into an aspirated fluid receiving chamber of the secondary cassette. Hence, fluids are suctioned out of the eye into the secondary cassette. When the procedure is completed, the contaminated secondary cassette, associated tubing and cutter are discarded.

Note that the secondary cassette includes a pair of spaced apart eyelets protruding away from a top cap portion to permit the secondary cassette to be hung from mating hanging hooks or prongs of the primary cassette. Also, the secondary cassette can be formed to provide a sealed container of any desirable cross section, such as circular or square, for example. The top cap portion of the secondary cassette, in one embodiment is provided with a secondary aspirator port, and a secondary vacuum port. A bottom cap of the secondary cassette can be provided with a drain or sampling third port in another embodiment of the invention.

In each of the above-described embodiments of the invention, for another and preferred embodiment, the secondary cassette includes a housing consisting of transparent material. As a result, a user can observe the amount of aspirating fluid drawn into the secondary cassette at any given time. Note that in certain applications, the secondary cassette can consist of opaque material.

BRIEF DESCRIPTION OF THE DRAWINGS

Various embodiments of the present invention will now be described with reference to the drawings, in which like items are identified by the same reference designation, wherein.

DETAILED DESCRIPTION OF THE INVENTION

Figure 2:
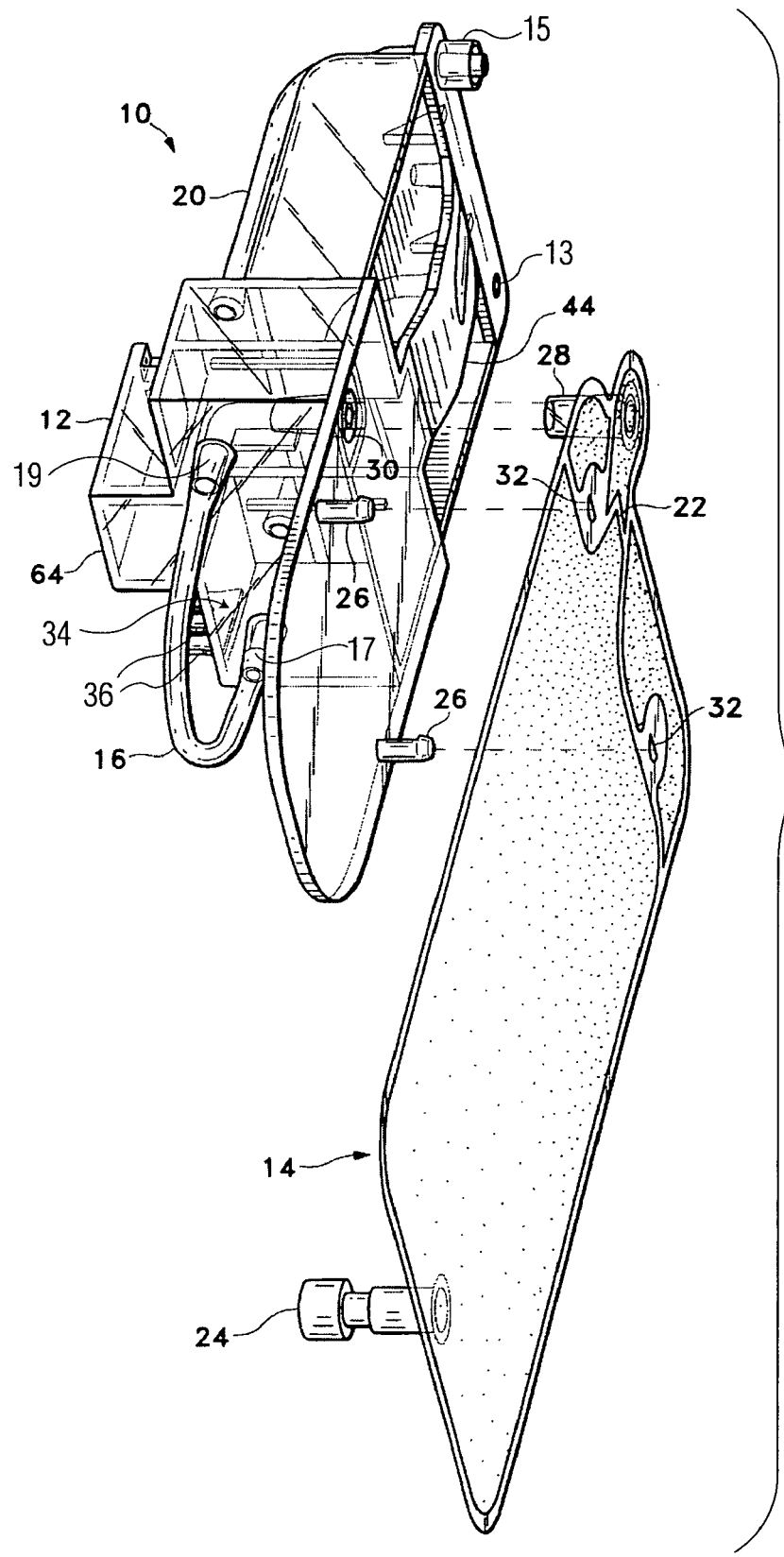
FIG. 2 is an exploded perspective or pictorial of the cassette of FIG. 1 in association with a drain bag.
Figure 3:
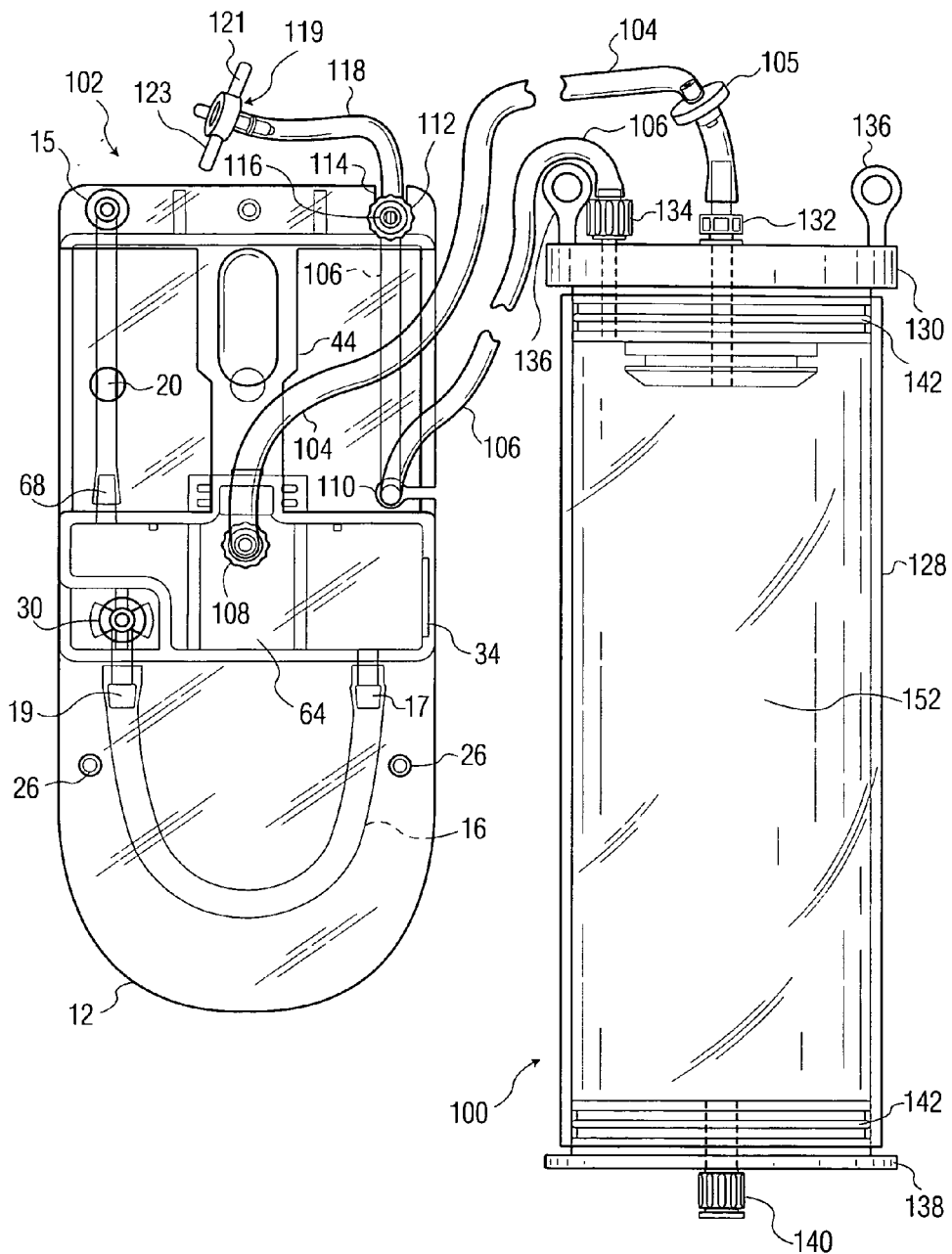
FIG. 3 is a front elevational view of a first embodiment of the invention showing a modified primary cassette, connected by tubing to a secondary cassette.
Figure 9:
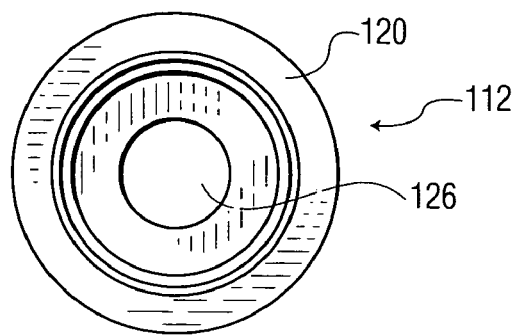
FIGS. 9, 10, and 11 show top plan, right side elevational, and bottom plan views, respectively, of a luer port device for another embodiment of the invention.
Figure 10:
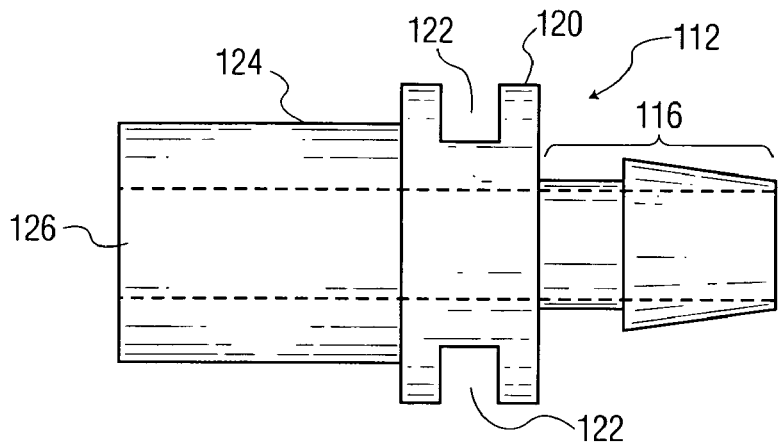
Figure 11:
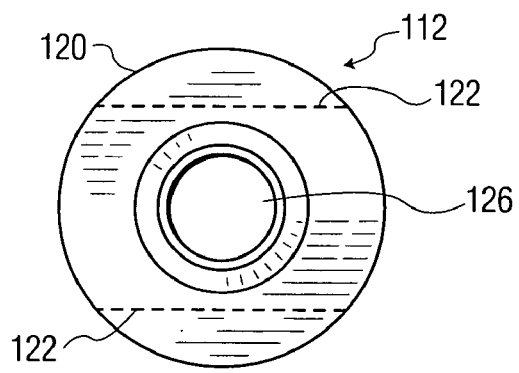

In FIG. 3, a first embodiment of the invention is shown that includes a disposable aspirator cassette 100 attached to a modified Alcon cassette 102 via flexible plastic tubing 104 and 106, (to be described in greater detail below). Through experimentation, the present inventors discovered that the primary cassette 10 shown in FIGS. 1 and 2, required modification to permit use of the disposable aspirator cassette 100 therewith. More specifically, the Alcon cassette 10 of FIGS. 1 and 2 was modified by installing a vacuum port 108 in a front portion of chamber 64. Also, vacuum port 66 has been sealed off and cut down. A keyhole 110 is cut into the side of housing 12 in the area where vacuum port 66 was formerly located, for retaining a portion of tubing 106, as shown. Aspiration line 18 of the prior cassette 10 has been eliminated, and a modified vacuum and/or aspirator port 112 with an end of tubing 106 attached thereto is removably installed in the position where the former first vacuum input port 13 was located. To accomplish the latter modification, a U-shaped slotway 114 has been cut into the top edge portion of housing 12 where port 13 was formerly located. The port 112 is provided by a specially designed snap-in Luer Lock as shown in FIGS. 9 through 11. As shown in the latter figures, the port 112 includes a front portion 116 for connection to an end of aspirator tubing 118 associated with a vitreous cutter handpiece (not shown). A circular central portion 120 of port 112 includes an opposing pair of centrally located grooves 122, as shown. The back portion of port 112 is circular for receiving an end of tubing 106 (see FIGS. 3 and 4). A throughhole 126 (see FIGS. 9-11) is provided in the port 112, as shown. The grooves 122 of port 112 provide a friction tight fit within the U-shaped slotway 114, as shown, for retaining port 112. The modified Alcon cassette 102 has been modified in a manner to permit it to operate substantially identically with its associated vitrectomy unit (not shown) as an unmodified Alcon cassette 10.

In an alternative embodiment, the modification of cassette 10 can be accomplished by leaving port 66, input port 13, and tubing 18 in place. Tubing 20 would then be removed, port 68 sealed off and cut down, a keyhole 110 located where port 68 was positioned, vacuum port 15 eliminated, and the U-shaped slotway 114 cut into the former location of vacuum port 15. As in the previous embodiment, the modified vacuum and or aspirator port 112 will now be located in slotway 114 in the former location of vacuum port 15. Otherwise, the alternative embodiment is utilized as described below for the former embodiment.

Figure 4:
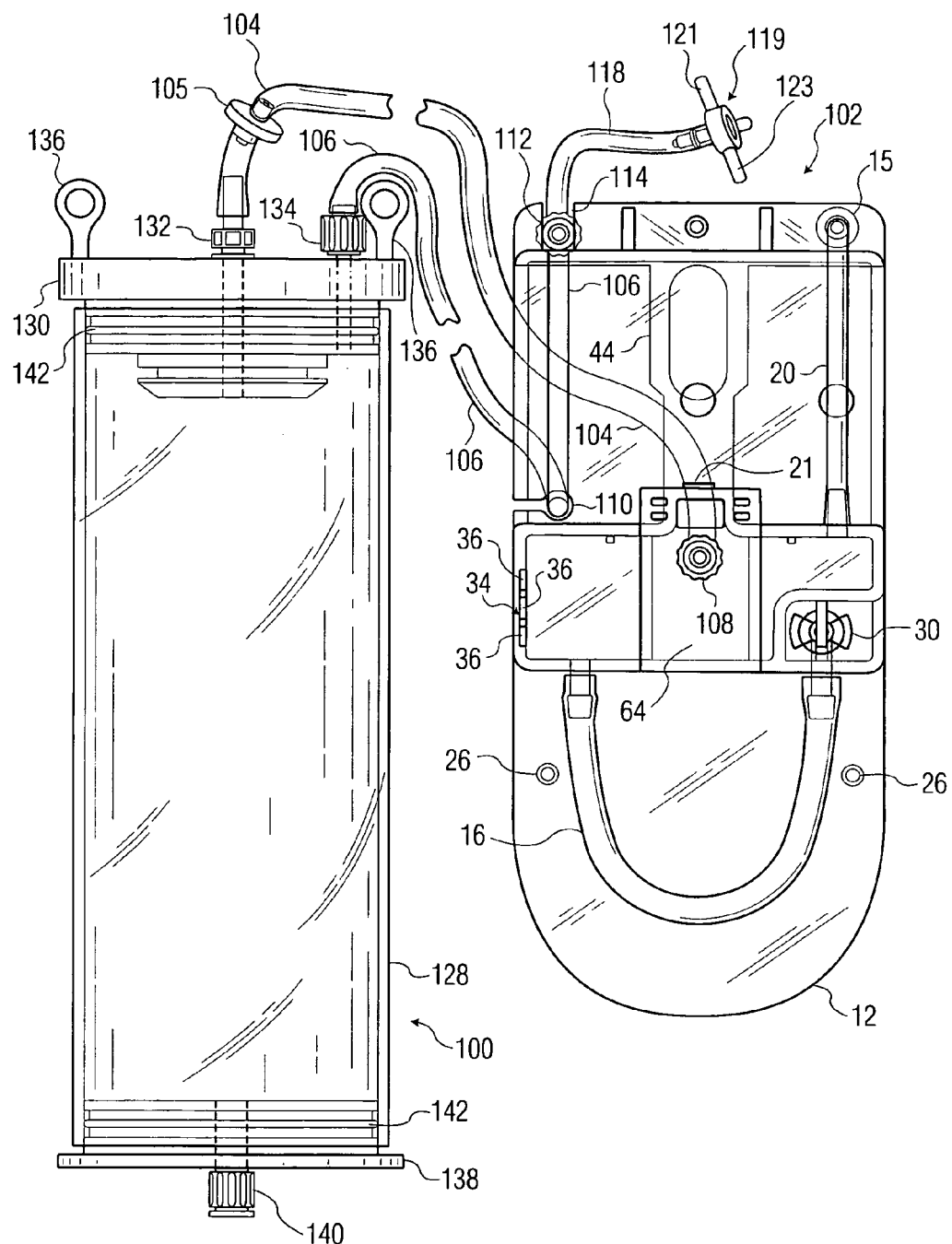
FIG. 4 is back elevational view of the front embodiment of the invention of FIG. 3.
Figure 5:
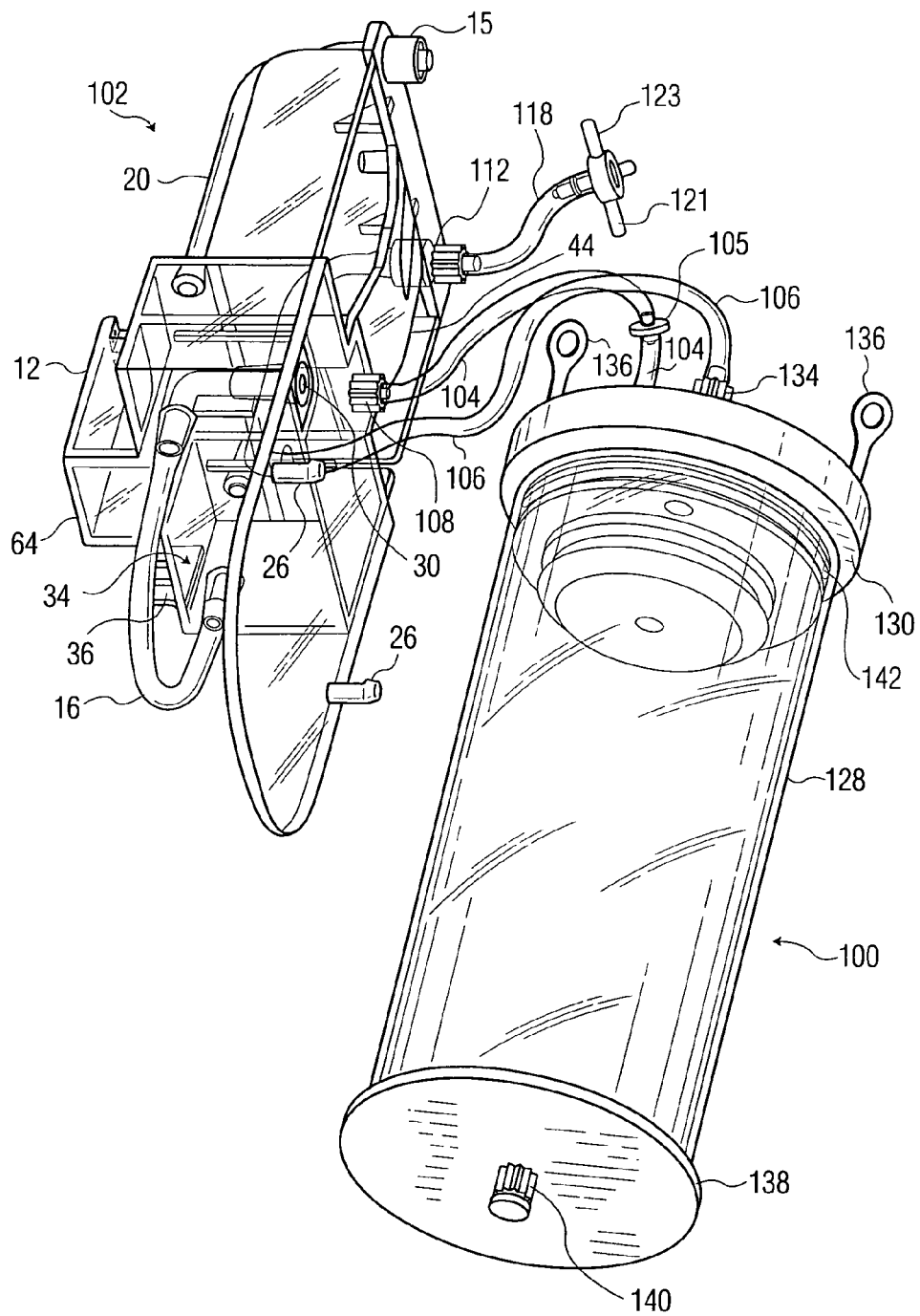
FIG. 5 is a pictorial view of the embodiment of the invention relative to FIG. 3 looking at an angle toward the front of the modified primary cassette with the secondary cassette spaced therefrom.
Figure 6:
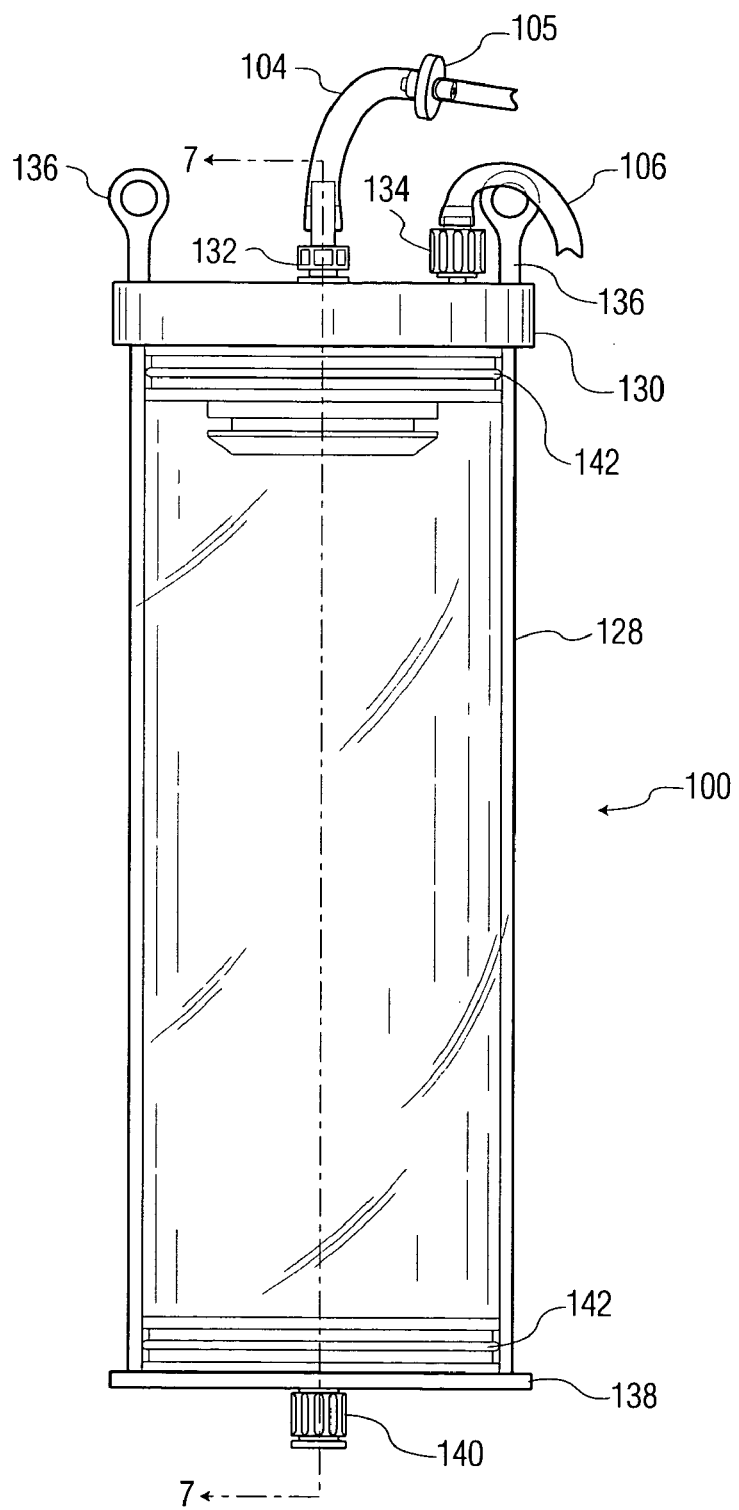
FIG. 6 is a back elevational view of the secondary cassette for the first embodiment of the invention.
Figure 7:
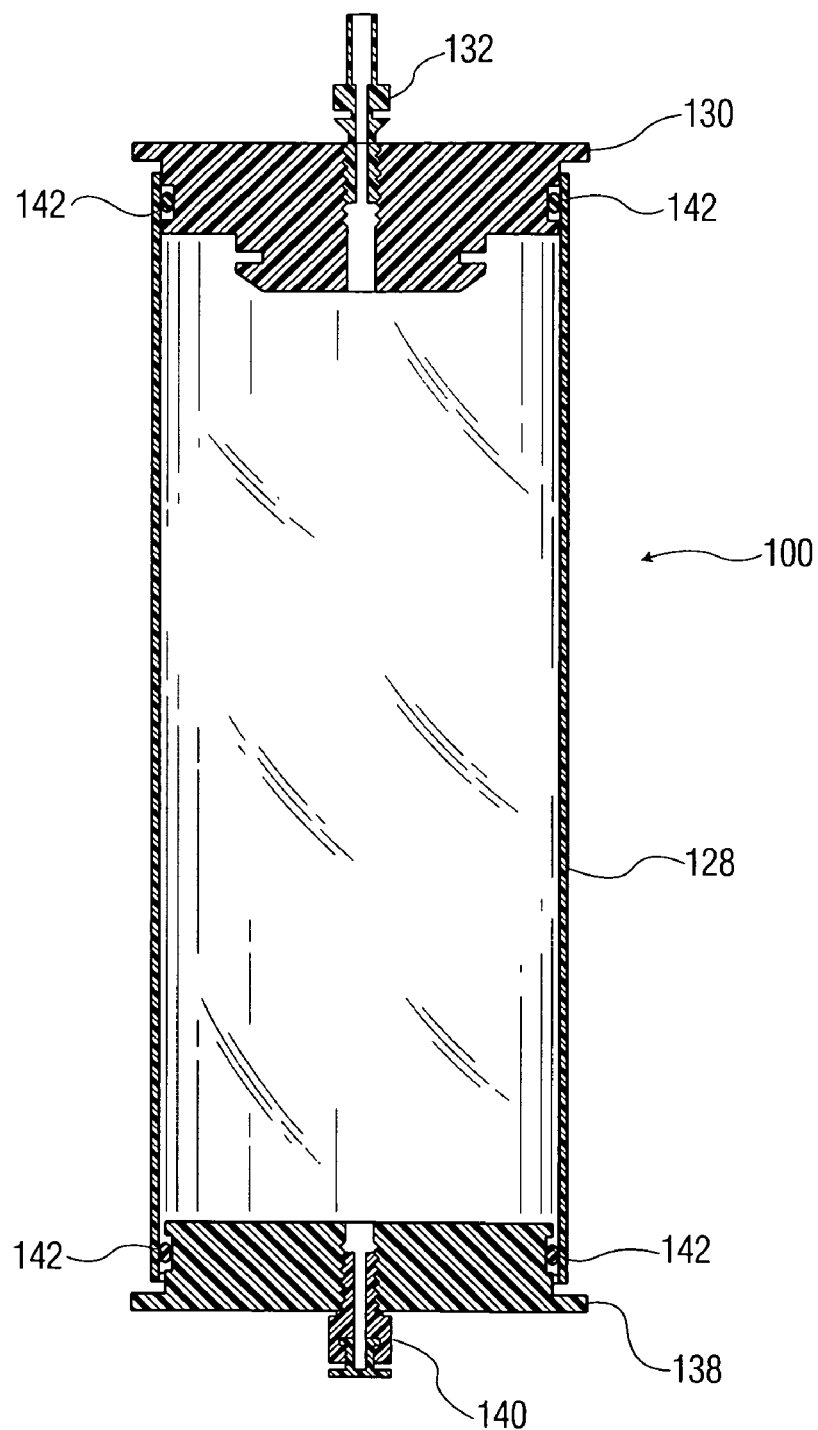
FIG. 7 is a cross-sectional view taken along 7-7 of the secondary cassette of FIG. 6.

With further reference to FIG. 3, and to FIGS. 4, 5, and 6, the modified Alcon cassette 102 represents a primary cassette, whereas the disposable cassette 100 represents a secondary aspirator cassette. As shown, the disposable cassette, in one embodiment of the invention, includes a cylindrical or tubular housing 128. One end of the housing 128 is sealed off by a top cap 130 that includes a centrally located secondary vacuum port 132 for connection via tubing 104 to the vacuum port 108 of the modified primary cassette 102. Also included in the top cap 130 is a secondary aspirator port 134 spaced away from port 132, the former being connected via tubing 106 to the aspirator port 112 of the modified Alcon primary cassette 102 as shown. A pair of spaced apart eyelets 136 are provided on the top cap 130 nears its circumferential edge for permitting the temporary or disposal aspirator cassette 100 to be hung from the hooks 26 of the primary cassette 102 during use. The other end of the secondary cassette 100 is sealed off by a bottom cap 138. In this example, the bottom cap 138 is provided with a centrally located drain or sample port 140. As shown in FIGS. 3 through 7, O-ring seals 142 are incorporated in the top end cap 130 and bottom end cap 138 for providing a vacuum tight seal for secondary cassette 100, and for securing the associated end caps thereto. Note that the illustration of O-ring seals 142 is not meant to be limiting, whereby any other suitable sealing means can be used. Note also that the use of eyelets 136 for hanging cassette 100 is not meant to be limiting, in that many other mechanisms can be used to support cassette 100, even laying it on a table.

Figure 1:
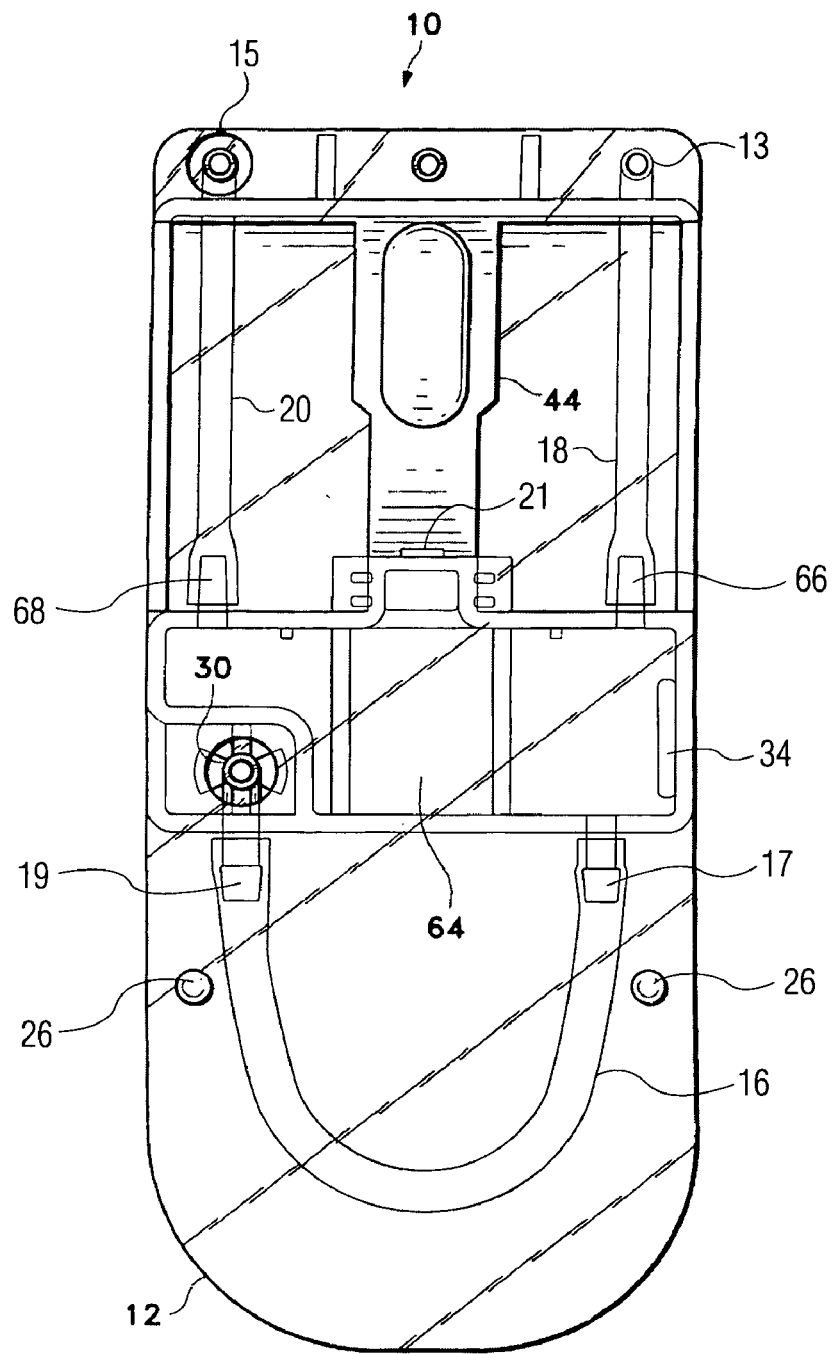
FIG. 1 is a front elevational view of a cassette in the prior art.

With reference to FIGS. 1 and 3, as previously indicated, the primary cassette 10 of FIG. 1 is modified, as shown in FIG. 3 as modified cassette 102, by removing the original aspiration line 18, cutting off and plugging the vacuum port 66, cutting the keyhole 110 into the housing 12, and cutting the U-shaped slotway 114 into the top portion of the housing 12 where the first vacuum input port 13 was previously located, and is now eliminated. With the primary aspirator port 112 installed in the U-shape slotway 114, as previously described, the taut top half portion of the tubing 106 between the aspirator port 112 and the keyhole 110 is identically located as the previously described aspiration line 18. As a result, when the modified primary cassette 102 is plugged into the associated vitrectomy unit, the latter unit is then operative to control pinch valves (not shown) to pinch off a top section of the tubing 106 for preventing further suction of aspirated fluid from the vitreous cutter handpiece, when such action is required by the ophthalmic surgeon.

Figure 8:
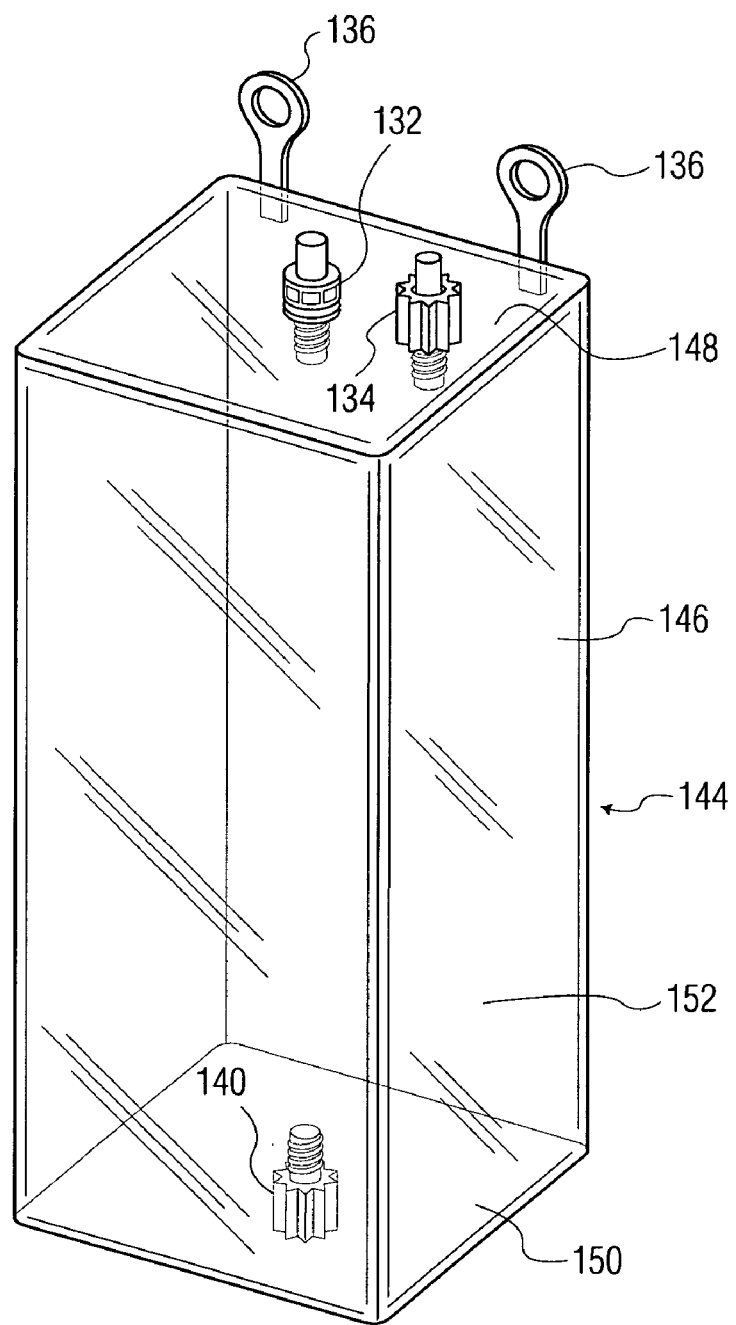
FIG. 8 is a pictorial view of a secondary cassette for another embodiment of the invention.

FIG. 8 shows an alternative embodiment for the invention that includes a rectangular or square shaped disposable secondary or aspirator cassette 144. The housing 146 is shown to have a rectangular or square shape, but alternatively can have any desired shape. In this alternative embodiment, the ends of the housing are sealed off by a non-removal top cap 148, and non-removal bottom cap 150. Otherwise, this alternative embodiment includes eyelets 136, centrally located secondary vacuum port 132, a secondary aspirator port 134, and a drain or sample port 140, each being employed for use as previously described for the first embodiment of the invention described above.

The materials used for the various embodiments of the invention will now be described for purposes of example, and are not meant to be limiting, that any other suitable materials can be used. The housing 128 for the first embodiment of the invention, housing 146 for the second embodiment of the invention, and the top cap and bottom cap 148, 150, respectively, for the second embodiment of the invention typically consist of any suitable transparent material such as Plexiglas, for example. The end caps 130 and 138 for the first embodiment of the invention associated with the secondary cassette 100 can consist of any suitable material, such as Delrin®. The flexible plastic tubings 104, and 106 are preferably provided by any suitable relatively transparent plastic tubing, but can otherwise be opaque if preferred.

With further reference to FIGS. 3 through 6, a three-way stopcock 119 is installed in one embodiment of the invention in aspirator tubing 118. The ports 121 and 123 can be used to selectively connect a vitreous cutter handpiece (not shown) and/or an extrusion needle (not shown) to aspirator tubing 118. Note that other ophthalmic surgical devices can be connected to aspirator tubing 118, in that the invention is not meant to be limited to use with vitreous cutters and/or extrusion needles. Also, in another embodiment of the invention, a hydrophobic and/or pathogen filter 105 is connected in the fluid path of tubing 104 to both filter air sucked into chamber 64 of cassette 102, and to block the flow of liquid and/or biological contaminants from aspirator cassette 100 into chamber 64.

Operation of the present invention will now be described. In the preferred embodiment of the invention, before connections from the secondary cassette 100 are made to the modified primary cassette 102, keyhole 110 and slotway 114 of the latter are open or free of any attachments or components. The secondary cassette 100 is provided as a subassembly with an end of tubing 104 attached to secondary vacuum port 132, and an end of tubing 106 attached to aspirator port 134 (see FIGS. 3, 4, and 5). Filter 105 is installed in tubing 104 as shown, and the other end of tubing 104 is free. The other end of tubing 106 is connected to the primary aspirator port 112, via mating luer connections (not shown). Aspirator tubing 118 has one end connected to aspirator port 112, and its other end connected to the three-way stopcock 119. The free end of tubing 104 is connected to a male or female luer connector for later connection to a mating luer connection (not shown) of vacuum port 108 of primary cassette 102. The provision of this subassembly facilitates the rapid attachment or connection of the secondary cassette 100 by hospital personnel to the primary cassette 102. More specifically, the interconnection therebetween is made by installing aspirator port 112 in slotway 114 of primary cassette 102, pulling tubing 106 taut between port 112 and keyhole 110, and pushing apportion of tubing 106 into keyhole 110 of primary cassette 102 for secure retention therein, thereby retaining tubing 106 taut. The luer connector on the free end of tubing 104 is connected to the mating luer connector of vacuum port 108 of primary cassette 102. Following this, the disposable secondary cassette 100 or 144 is then installed via its' eyelets 136 onto the hooks 26 protruding from the modified primary cassette 102 (see FIGS. 3-5). Also, before installing the disposable secondary cassette 100 or 144, one must be sure that the drain or sample port 140 is closed. The modified primary cassette 102 is installed onto its associated vitrectomy unit. Next, a vitreous cutter handpiece (not shown), and/or an extrusion needle (not shown) are connected via associated tubing (not shown) to ports 121 and 123 of three-way stopcock 119.

Once the associated vitrectomy unit (not shown) is turned on, it will rotate a cam wheel against peristaltic pump tube 16 of primary cassette 102. The vitrectomy unit connects a vacuum source to vacuum input port 21, thereby creating a vacuum in chamber 64, and in the interior receiving chamber 152 of the associated secondary cassette 100 or 144. The vacuum created within the chamber 152 of the associated secondary cassette 100 or 144 will in turn cause aspirated fluid from the vitreous cutter (not shown) and/or the extrusion needle (not shown) to be drawn from tubing 118, through tubing 106, and port 134 into the aspirated fluid receiving chamber 152 of the associated secondary cassette 100 or 144. When the operation is completed, the vitrectomy unit is turned off, the vitreous cutter handpiece and/or the extrusion needle, along with the subassembly including associated aspirator tubing 118, aspirator port 112, and tubing 106 and 104 are removed from the primary cassette 102, and discarded along with the secondary aspirator cassette 100 or 144. In preparation for the next operation, a new disposable secondary cassette 100 or 144, in this example, provided as a subassembly as described above, is installed as previously described for initiating the next operation. In other words, all of the components contaminated by aspirated fluid are discarded. In this manner, the primary cassette 102 can be reused indefinitely until such time that it may develop a defect.

Note that the secondary cassettes 100, 144 of FIG. 3, respectively, are shown with tubing 104 and 106 attached, each connected at one end to ports 132 and 134, respectively. As described for the preferred embodiment of the invention, various connection tubings are luer connections. However, in alternative embodiments, the connections can be via any suitable connections or attachments. For example, it is expected that for production versions of secondary cassettes 100, 144, that non-removable tubing barbs will be used, thereon.

Note further that typically disposable vitreous cutters and/or extrusion needles are expected to be used. However, if any such devices used are reusable, after a given operation, they will be removed, sterilized, and provided for later reuse.

Although various embodiments of the invention have been shown and described, they are not meant to be limiting. Those of skill in the art may recognize certain modifications to these embodiments, which modifications are meant to be covered by the spirit and scope of the appended claims. For example, although various materials have been indicated for purposes of example for use in the present invention, any other suitable materials can be utilized.

What we claim is:

1. A disposable cassette system for use with an existing vitrectomy unit, comprising:
    a primary cassette associated with said vitrectomy unit, said primary cassette including a vacuum chamber, whereby when said primary cassette is plugged into said vitrectomy unit, interactive means therebetween produces a vacuum in said vacuum chamber;
    a secondary cassette including a sealed aspirated fluid receiving chamber;
    means for connecting said vacuum chamber of said primary cassette to said aspirated fluid receiving chamber of said secondary cassette, for producing a vacuum in the latter whenever a vacuum is produced in the former;
    means for directly connecting during surgery at least one ophthalmic surgical device to the aspirated fluid receiving chamber of said secondary cassette, whereby aspirated fluid is drawn from ophthalmic surgical device into said chamber whenever a vacuum is present therein, and
    means included in said vacuum chamber connecting means for blocking the flow of aspirated fluid from said secondary cassette into said primary cassette, thereby keeping said primary cassette free of contamination from said aspirated fluid to permit reuse of the primary cassette in successive surgeries, and disposal of the contaminated said secondary cassette after each surgery.

2. The disposable cassette system of claim 1, wherein said blocking means includes a filter.

3. An aspirator cassette system comprising:
    a reusable primary cassette including:
        a housing;
        means integral to a front portion of said housing for plugging said primary cassette into and activating an associated vitrectomy unit;
        a vacuum chamber formed in a central portion of said housing;
        means for forming a vacuum within said vacuum chamber upon activation of said vitrectomy unit;
        a primary vacuum port installed on said vacuum chamber;
        a keyhole formed into and proximate a side edge portion of said housing, and located above and proximate said vacuum chamber;
        a slotway formed in a top edge portion of said housing in vertical alignment with and spaced away from said keyhole; and
        a primary aspirator port removably secured within said slotway of said housing, for providing a connection to one end of an aspirator tube;
        means for connecting another end of said aspirator tube to at least one ophthalmic surgical device;
    a disposable secondary cassette including:
        a housing containing an aspirated fluid receiving chamber therein, a sealed top end, and a sealed bottom end;
        a secondary vacuum port installed in the top end of said housing for accessing the fluid receiving chamber; and
        a secondary aspirator port installed in the top end of said housing for accessing the fluid receiving chamber;
    first tubing connected between said primary vacuum port, and said secondary vacuum port, for causing a vacuum to be provided in said aspirated fluid receiving chamber of said secondary cassette, whenever a vacuum is formed in said vacuum chamber of said primary cassette; and
    second tubing connected between said primary aspirator port and said secondary aspirator port, said second tubing having a portion tautly secured on a back portion of said primary cassette housing between said keyhole retention slot and said primary aspirator port, whereby upon said primary cassette activating an associated vitrectomy unit, with said at least one ophthalmic surgical device connected to said primary aspirator port, aspirated fluid from at least one ophthalmic surgical device is drawn through said primary aspirator port, said second tubing, and said secondary aspirator port for deposit into said aspirated fluid receiving chamber of said secondary cassette, thereby bypassing and preventing contamination of said primary cassette with aspirated fluid, permitting reuse of said primary cassette upon installation of a new primary aspirator port.

4. The system of claim 3, further including:
a pair of spaced apart hanging hooks on a front portion of the housing of said primary cassette; and
a pair of spaced apart eyelets protruding from the top end of said housing of said secondary cassette, for permitting said secondary cassette to be hung from the hanging hooks of said primary cassette.

5. The system of claim 3, wherein the housing of said secondary cassette has a circular cross section.

6. The system of claim 5, further including:
top and bottom caps for sealing off the top and bottom ends, respectively, of the housing of said secondary cassette.

7. The system of claim 3, further including a drain or sample port in the bottom end of the housing of said secondary cassette.

8. The system of claim 3, wherein the housing of said secondary cassette has a square cross section.

9. A disposable aspirator cassette system, comprising:
an existing primary cassette modified to eliminate contamination thereof during use in surgery to permit reuse thereof, the modified said primary cassette including:
a vacuum chamber;
a primary vacuum port installed in a front wall of said vacuum chamber, said primary vacuum port including a filter;
a slotway formed in a top portion of said primary cassette;
a keyhole tubing retention slot located in a mid-portion of said primary cassette spaced from and opposing said aspirator port above said vacuum chamber; and
a disposable secondary cassette including:
a housing containing an aspirated fluid receiving chamber therein, a sealed top end, and a sealed bottom end;
a secondary vacuum port installed in the top end of said housing for accessing the fluid receiving chamber; and
a secondary aspirator port installed in the top end of said housing for accessing the fluid receiving chamber;
first tubing connected between said primary vacuum port, and said secondary vacuum port;
a primary aspirator port adapted for removable securement in said slotway of said primary cassette;
second tubing connected between said primary aspirator port and said secondary aspirator port, said second tubing having a portion secured in said keyhole tubing retention slot for maintaining a portion of the tubing taut on a back portion of said primary cassette between the slot and a said primary aspirator port installed in said slotway of said primary cassette;
said primary cassette being adapted for plugging into and activating an associated vitrectomy unit, thereby causing a vacuum to be formed in said vacuum chamber, in turn causing a vacuum to be formed in the aspirated fluid receiving chamber of said secondary cassette, whereby when an ophthalmic surgical device is connected to said primary aspirator port, aspirated fluid is drawn from said ophthalmic surgical device through said primary aspirator port, said second tubing, and said secondary aspirator port into the aspirated fluid receiving chamber of said disposable secondary cassette.

10. The disposable aspirator cassette system of claim 9, wherein said primary cassette further includes:
a pair of spaced apart hanging hooks located below the first wall of said vacuum chamber.

11. The disposable aspirator cassette system of claim 10, wherein said secondary cassette further includes:
a pair of spaced apart eyelets installed in the top end of said housing, for hanging said secondary cassette from the hanging hooks of said primary cassette; and
a drain or sample port installed in the bottom end of said housing, for selectively draining fluid from said fluid receiving chamber.

12. The disposable aspirator cassette system of claim 9, further comprises a disposable subassembly packaged to include:
said disposable secondary cassette;
said first tubing having one end connected to said secondary vacuum port, and a free end;
said second tubing having one end connected to said secondary aspirator port, and another end connected to said primary aspirator port; and
said disposable subassembly is connected to said primary cassette by installing said primary aspirator port into said slotway, a portion of said second tubing into said keyhole tubing retention slot, and the free end of said first tubing to said primary vacuum port, whereby after a surgery use, said disposable subassembly is disconnected from said primary cassette along with said ophthalmic surgical device and discarded.

13. The disposable aspirator cassette system of claim 9, further including a filter in said second tubing.

14. The disposable aspirator cassette system of claim 12, further including a filter in said second tubing.

15. The disposable aspirator cassette system of claim 9, further including a three-way stopcock connected directly to said primary aspirator port, for connecting via said stopcock either one or both of a vitreous cutter and an extrusion needle to said aspirator port.

16. The disposable aspirator cassette system of claim 12, said disposable subassembly further including a three-way stopcock connected directly to said primary aspirator port, for connecting via said stopcock either one or both of a vitreous cutter and an extrusion needle to said aspirator port.

* * * * *